(12) United States Patent
Satomi et al.

(10) Patent No.: US 8,883,307 B2
(45) Date of Patent: Nov. 11, 2014

(54) SPHERICAL PARTICLE OF CRYSTALLINE MANNITOL

(75) Inventors: Jin Satomi, Fuji (JP); Maki Inaba, Shizuoka (JP)

(73) Assignee: Mitsubishi Shoji Foodtech Co., Ltd., Tokyo (JP)

( * ) Notice: Subject to any disclaimer, the term of this patent is extended or adjusted under 35 U.S.C. 154(b) by 0 days.

(21) Appl. No.: 12/451,667

(22) PCT Filed: May 9, 2008

(86) PCT No.: PCT/JP2008/058646
§ 371 (c)(1),
(2), (4) Date: Nov. 24, 2009

(87) PCT Pub. No.: WO2008/146590
PCT Pub. Date: Dec. 4, 2008

(65) Prior Publication Data
US 2010/0167052 A1    Jul. 1, 2010

(30) Foreign Application Priority Data

May 28, 2007 (JP) ................................ 2007-140923

(51) Int. Cl.
| | |
|---|---|
| B32B 5/16 | (2006.01) |
| A23L 1/236 | (2006.01) |
| A61K 47/10 | (2006.01) |
| A23L 1/09 | (2006.01) |
| C07H 3/02 | (2006.01) |
| A61K 9/14 | (2006.01) |
| C13B 30/02 | (2011.01) |

(52) U.S. Cl.
CPC ................ *A23L 1/2364* (2013.01); *A61K 47/10* (2013.01); *A23L 1/097* (2013.01); *C07H 3/02* (2013.01); *A61K 9/145* (2013.01); *C13B 30/02* (2013.01)
USPC .......................................... 428/402; 424/465

(58) Field of Classification Search
CPC ....... A23L 1/097; A23L 1/2364; C13B 30/02; A61K 47/10; A61K 9/145; C07H 3/02
USPC .......................................................... 428/402
See application file for complete search history.

(56) References Cited

U.S. PATENT DOCUMENTS

| | | | |
|---|---|---|---|
| 3,145,146 A | 8/1964 | Lieberman | |
| 5,958,471 A * | 9/1999 | Schwarz et al. | 426/3 |
| 6,264,989 B1 * | 7/2001 | Kato et al. | 424/490 |

FOREIGN PATENT DOCUMENTS

| | | | | |
|---|---|---|---|---|
| JP | 61-085330 A | 4/1986 | | |
| JP | 11092403 A * | 4/1999 | | A61K 47/36 |

(Continued)

OTHER PUBLICATIONS

Elversson, et al., "Particle Size and Density in Spray Drying-Effects of Carbohydrate Properties", Journal of Pharmaceutical Sciences, vol. 94, No. 9, Sep. 2005, pp. 2049-2060.*

(Continued)

*Primary Examiner* — Gary Harris
(74) *Attorney, Agent, or Firm* — Rader, Fishman & Grauer PLLC

(57) ABSTRACT

[Summary]
[Problems] To provide extremely-spherical-three-dimensional-shaped particles of crystalline mannitol containing large hollows and gaps inside.
[Solution] Spherical particles of crystalline mannitol made by spray drying, extremely spherical (having an aspect ratio of 1.0 to 1.2), high oil absorption rates according to test method A, wherein powder has a mean particle diameter of 15 to 165 μm, a loose bulk density of 0.35 to 0.60 and an angle of repose of 30 to 50 degrees, and has a hardness of 7 to 20 kgf, when directly compressed.

8 Claims, 1 Drawing Sheet

(56) References Cited

FOREIGN PATENT DOCUMENTS

| | | | | |
|---|---|---|---|---|
| JP | 2001-010979 | A | | 1/2001 |
| JP | 3491887 | B2 | | 1/2001 |
| JP | 2001010979 | A * | 1/2001 | ............ A61K 47/10 |
| JP | 3447042 | B1 | | 7/2003 |
| JP | 2004-067670 | A | | 3/2004 |
| JP | 2006-028130 | A | | 2/2006 |
| JP | 3910939 | B2 | | 4/2007 |
| WO | WO-01/72285 | A1 | | 10/2001 |
| WO | WO-02/069934 | A1 | | 9/2002 |
| WO | WO-02/070013 | A1 | | 9/2002 |

OTHER PUBLICATIONS

PCT/ISA/210, PCT/JP2008/058646, May 28, 2008 (2 pages).
Communication from European Patent Office for application No. 087525291.1 dated May 10, 2012.

* cited by examiner

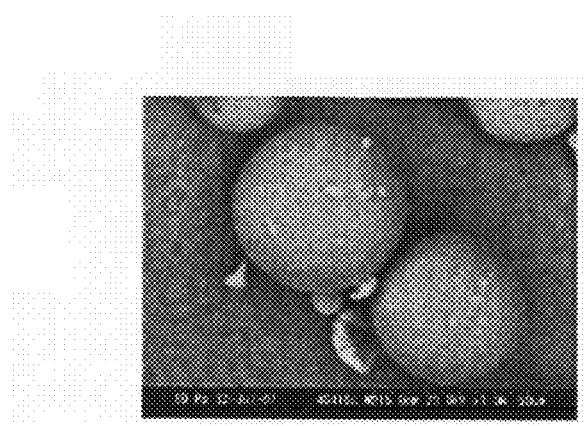
Invention 3
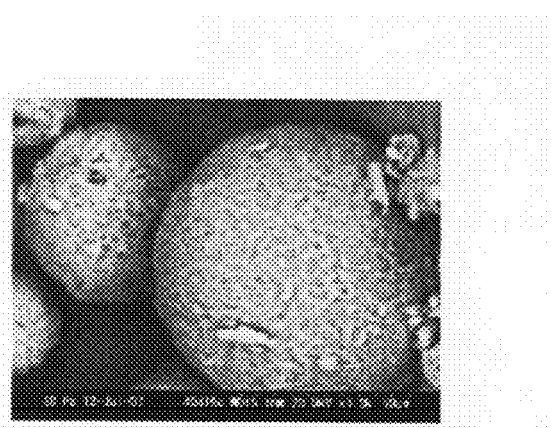
Invention 4
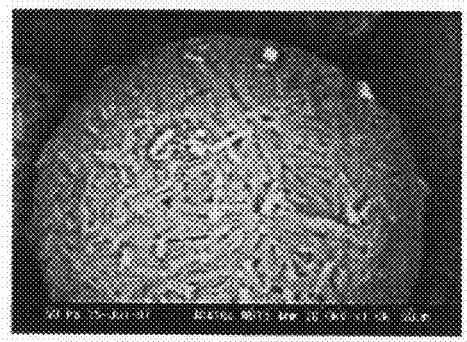
Invention 6
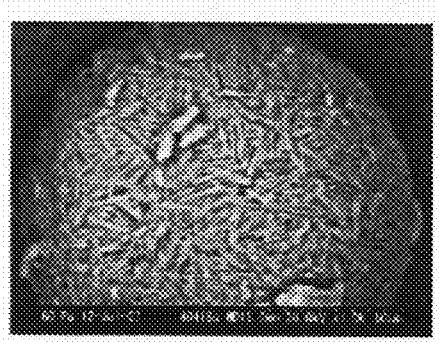
Invention 7
Control 1    Mannit P
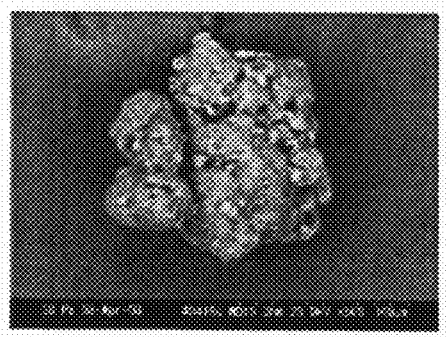
Control 2    Pearlitol 100SD
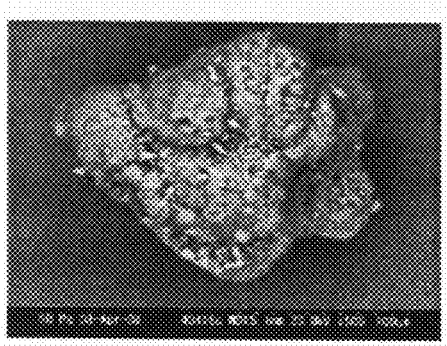
Control 3    Pearlitol 200SD
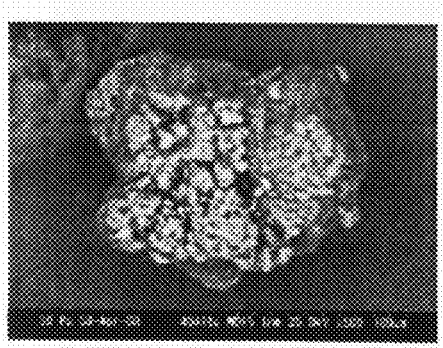
Control 4    Parteck M200

SPHERICAL PARTICLE OF CRYSTALLINE MANNITOL

TECHNICAL FIELD

The present invention relates to highly spherical particle of crystalline mannitol useful as material to make food, medicines, etc.

BACKGROUND ART

D-mannitol, a kind of hexitol, is widely used in a variety of foods, base for various medicines or excipient for tablets, powder, etc. thanks to its characteristics such as excellent stability, usually in inodorous white crystalline powder, mild sweet taste equivalent to 60 to 70% of sucrose, lower calorie than sucrose or glucose, safety to human body, etc.

Mannitol takes the form of fine needle-like crystals, when crystallized from water solution, and is poorly fluid as granulated. In addition, mannitol, often marketed and used in the form of fine crystalline powder commonly packed in kraft bag, is likely to get consolidated, when distributed or stocked, significantly losing its commercial importance.

Moreover, other problems are found e.g. in the fact that tablets, made from crystalline mannitol just as crystallized from water solution and directly compressed, are easily collapsed due to low hardness or it is difficult to be compressed successively as disturbed by capping, sticking etc. during the process of compressing.

To overcome the above drawbacks of crystalline mannitol, various solutions have been so far proposed.

One of the solutions is to work it into balls in order to improve fluidity, while avoiding consolidating or collapsing, as reported with some examples.

Japanese Patent No. 3447042 discloses "A manufacturing process of spherical particles having an aspect ratio of 1.2 or less, apparent density of 0.65 g/ml or more in aggregate, an angle of repose equal to or less than 35 degrees and abrasiveness of 1.0 or less, wherein particles containing 95% by weight or more water-soluble single matter having a viscosity of 10 cP or less in saturated water solution are made", referring to D-mannitol as an example of "water-soluble single matter".

Japanese Patent No. 3491887 discloses "A manufacturing process of sugar alcohol granulated aggregate, to be subjected to direct compression processing, containing 95% by weight or more particles of 710 µm or less, 50% by weight or more particles within a range of 75 to 710 µm, having an apparent density of 0.5 g/ml or more, an angle of repose equal to or less than 40 degrees, wherein powder containing 95% or more by weight sugar alcohol is put into a fluidized granulation coating device, while supplied with fluidized air into the container to fluidize the powder, spraying sugar alcohol water solution to make particles, followed by sifting the granulated matters through a sieve", referring to D-mannitol as an example of "sugar alcohol".

Japanese Patent No. 3910939 discloses "Spherical particles, made of particles containing 95% by weight or more water-soluble single matter, having an aspect ratio of 1.2 or less, apparent density of 0.65 g/ml or more in aggregate, an angle of repose equal to or less than 35 degrees, characterized in that a) the water-soluble single matter is selected as one of the group consisting of sugar alcohol, vitamin C and sodium chloride; b) saturated water solution of the water-soluble single matter has a viscosity of 10 cP or less in the range of 25 to 45° C.; and c) the spherical particles have abrasiveness of 1.0% or less", referring to D-mannitol as an example of "sugar alcohol".

However, granulation is the only processing method adopted in all of the above 3 patents, leaving various problems unsolved.

Granulation consists in coagulating one after another the surrounding mannitol particles around the core mannitol, using appropriate solvent and solution, as needed, drying the surrounding to precipitate solid ingredients, or combining these methods, anyway to make the raw material powder grow into bigger and bigger clusters.

The problem of the above is that it is especially difficult and costly to form, by granulation, highly spherical particles having a fine diameter from needle-like crystals like crystalline mannitol, used as raw material powder, failing to respond to the needs of light and fine particles, since the particles thus obtained are heavy as charged with crystals dense inside the particles and likely to have a large particle diameter.

On the other hand, Japanese Laid-Open Patent No. 61-85330 discloses a manufacturing process of an excipient for a direct compressing tablet characterized in that D-mannitol is sprayed and dried. However, the Official Gazette describes the manufacturing conditions quite roughly, only referring to use of 25 to 33% by weight D-mannitol water solution and spraying and drying at discharging temperatures of 120 to 140° C., without any intention to obtain spherical powder. The photo of actually obtained powder as shown in FIG. 1 in the Official Gazette shows the distorted shape, far from sphericity.

[Patent Document 1] Specification of Japanese Patent No. 3447042

[Patent Document 2] Specification of Japanese Patent No. 3491887

[Patent Document 3] Specification of Japanese Patent No. 3910939

[Patent Document 4] Japanese Laid-Open Patent No. 61-85330

DISCLOSURE OF THE INVENTION

Problems to be Solved by the Invention

One of the major applications expected of mannitol is the role of vehicle to carry bioactive substances. In that case, bioactive ingredients need to be held usually in fine particles of mannitol. The fluidized or agitated granulation is adopted as a processing method. Therefore, mannitol should preferably be characterized by 1) high oil absorption rate and high sphericity to absorb and hold the active ingredients, 2) low apparent density at the same time to have light and easily floating and fluidized particles when processed, 3) high hardness obtained when directly compressed to have sufficient tablet hardness when compressed.

The object of the present invention is to provide highly spherical mannitol particles, with large cavities inside the particles, the most absorbent of oil, as could never been found in the conventional particles or granules, excellent in fluidity, sufficiently hardened when directly compressed, on overcoming the various drawbacks of the conventional mannitol spherical particles and directly compressible mannitol powder.

Means to Solve the Problems

Working hard to attain the above objects, the present inventors found out that some of mannitol particles, obtained by fine-tuning the crystallization speed and water content evaporation speed, are extremely highly spherical, highly absorbent of oil, with a low apparent density, sufficiently hard when directly compressed, thereby accomplishing the present invention. In other words, the present invention solves the problems by means of the following.

First, spherical particle of crystalline mannitol having an aspect ratio of 1.0 to 1.2, an oil absorption rate 1 of 25 to 60% and an oil absorption rate 2 of 15 to 40% according to test method A.

Second, spherical particle of crystalline mannitol, as described in the above first, having a mean particle diameter of 15 to 165 μm and a loose bulk density of 0.35 to 0.60 in powder.

Third, spherical particle of crystalline mannitol, as described in the above first or second, having a mean particle diameter of 15 to 165 μm and an angle of repose equal to 30 to 50 degrees.

Fourth, spherical particle of crystalline mannitol, as described in the above first, having a mean particle diameter of 15 to 85 μm and a loose bulk density of 0.35 to 0.60 in powder.

Fifth, spherical particle of crystalline mannitol, as described in the above first or fourth, having a mean particle diameter of 15 to 85 μm and an angle of repose equal to 30 to 50 degrees in powder.

Sixth, spherical particle of crystalline mannitol, as described in the above first, having a mean particle diameter of 15 to 65 μm and a loose bulk density of 0.35 to 0.60 in powder.

Seventh, spherical particle of crystalline mannitol, as described in the above first or sixth, having a mean particle diameter of 15 to 65 μm and an angle of repose equal to 30 to 50 degrees in powder.

Eighth, crystalline mannitol powder, as described in any of the above first to seventh, having a tablet hardness of 7 to 20 kgf, when directly compressed.

Ninth, spherical particle of crystalline mannitol, as described in the above first, having a mean particle diameter of 15 to 100 μm and a loose bulk density of 0.35 to 0.60 in powder and/or an angle of repose equal to 30 to 50 degrees.

Tenth, spherical particle of crystalline mannitol, as described in the above first, having a mean particle diameter of 15 to 85 μm and a loose bulk density of 0.35 to 0.60 in powder and/or an angle of repose equal to 30 to 50 degrees.

Eleventh, spherical particle of crystalline mannitol, as described in the above first, having a mean particle diameter of 15 to 65 μm and a loose bulk density of 0.35 to 0.60 in powder and/or an angle of repose equal to 30 to 50 degrees.

Twelfth, spherical particle of crystalline mannitol, as described in any of the above first to eleventh, containing 30% or more particles having a diameter smaller than 74 μm.

Then, the present invention relates also to crystalline mannitol powder, as described in any of the above first to twelfth, manufactured not by granulation but by spray drying.

The present invention relates to highly spherical particle of mannitol having powder characteristics such as higher oil absorption and lower apparent density than any conventional mannitol particles.

The present invention relates to highly spherical particle of crystalline mannitol, not only highly spherical but also three-dimensionally characterized by the presence of big cavities inside the particles, thereby enabling extremely high oil absorption.

The aspect ratio in the present invention means a ratio between the long and short axes of the particle, giving an index of sphericity. To determine the ratio between the long and short axes, a scanning electron microscope (S-2600N, produced by HITACHI, LTD.) was used to photograph 30 spherical particles, without metal vapor deposition, at an acceleration voltage of 20 kV, with vacuum of 50 Pa, under magnification of 1500 times, to measure the length of each long axis (long diameter) and that of each short axis (short diameter) vertically pulled from the midpoint of the long axis, to obtain the ratio of the long diameter to the short diameter about the 30 spherical particles, and to get the mean values among the 30 pieces.

The oil absorption rate according to test method A in the present invention is defined as follows. 30 g of middle chain fatty acid triglyceride (Coconad MT produced by KAO CORPORATION) and 15 g of mannitol as a sample are put in a glass beaker of 100 ml to be stirred with spatula gently enough to avoid crush of fine particles, followed by introducing it into a vacuum constant temperature dryer (VOS-300D, produced by EYELA) to impregnate it with oil for three hours at a room temperature at a pressure reduced down to 0.67 pascals.

Then, it is poured into a centrifuge tube (having openings at bottom) with a filter cloth of 325 meshes laid inside to centrifuge it by a centrifuge (H-500R, produced by KOKUSAN Co., Ltd.) for 10 minutes at about 1300 G. Then, the weight (Weight a) of the powder sample remaining in the centrifuge tube after centrifugation is obtained, on checking the measured values of the weight of the centrifuge tube containing the sample after centrifuged and the tare weight of the centrifuge tube, to regard as oil absorption rate 1 the value calculated by the following equation 1.

$$\text{Oil absorption rate } 1(\%) = [(\text{Weight } a - 15)/15] \times 100 \quad \text{(Equation 1)}$$

Moreover, in a glass beaker of 100 ml, the centrifuge tube containing the sample after centrifuged is put, 20 g of n-hexane is added onto the powder sample, followed by centrifuging it by a centrifuge for 10 minutes at about 1300 G. Then, the weight (Weight b) of the powder sample remaining in the centrifuge tube after centrifugation is obtained, on checking the measured values of the weight of the centrifuge tube containing the sample after centrifuged and the tare weight of the centrifuge tube, to regard as oil absorption rate 2 the value calculated by the following equation 2.

$$\text{Oil absorption rate } 2(\%) = [(\text{Weight } b - 15)/15] \times 100 \quad \text{(Equation 2)}$$

The mean particle diameter in the present invention is called in general a median diameter which gives 50% of fine particles totalizing distribution.

A laser diffraction particle size distribution measuring instrument MT-3000 (manufactured by NIKKISO CO., LTD.) and 2-propanol (reagent class 1, purity of 99.0% or more produced by Wako Pure Chemical Industries, Ltd.) as dispersion solvent are used in particle size distribution measurement. The sample is added till the instrument indicates that the quantity is proper, followed by perform ultrasonic processing for 30 seconds at an ultrasonic output of 40 W and then, measuring the mean particle diameter. These steps are taken twice repeatedly on a type of sample to obtain the mean value, which is regarded as a mean particle diameter. This opportunity is taken also to calculate the particle size distribution from the measured values.

The loose bulk density in the present invention is defined as a filled density when fine particles make a free fall inside a predetermined container, measured as in the following, using A.B.D powder characteristic measuring apparatus (produced by TSUTSUI SCIENTIFIC INSTRUMENTS CO., LTD.).

A sample container (capacity: 100 ml) is put on a stand. A sample is dropped on it from a sample hopper, from which the discharging nozzle has been detached, to fill the sample container till heaping, remove the heap over the top with spatula and measure the weight. The same steps are taken three times repeatedly on a type of sample to obtain the mean value, which is regarded as the loose bulk density.

The angle of repose in the present invention is defined as angle of a heap formed when fine particles make a free fall on a disk, measured by A.B.D powder characteristic measuring apparatus (manufactured by TSUTSUI SCIENTIFIC INSTRUMENTS CO., LTD.) as follows. A sample thrown into a sample hopper is dropped through a vibrating rod, net with a 1000 μm mesh, discharging funnel, nozzle having an inner diameter of 1 cm, onto a disk of a base for a sample of an angle of repose, to make a heap and measure the angle of the heap at three points different in direction. The same steps are taken three times repeatedly to obtain a mean value, which is regarded as an angle of repose.

The hardness, when directly compressed, in the present invention is defined as a mean value of hardness of 10 tablets of each sample compressed by a compressing machine (VIRG0512SS2AZ, manufactured by KIKUSUI SEISAKUSHO LTD.), at a compressing force of 1000 kgf to make tablets (having a weight of 200 mg, shaped flat 8 mmϕ, plain), using magnesium stearate as an outer lubricant, measured by a tablet hardness meter (Type: TH-203CP produced by Toyama Sangyo Co., Ltd.).

Spherical particles of crystalline mannitol of the present invention are obtained e.g. from mannitol water solution put into a spray dryer, strictly controlling the amount of introduced air and the temperature in order that drops of mannitol water solution released from an atomizer or a nozzle form a spherical shape, thanks to surface tension, to keep the shape as it is, at the time of precipitation of crystals or water evaporation. Keeping in balance the crystallization speed and water evaporation speed, crystals are precipitated from the surface of the liquid drops the first, the dilatation of spherical particles due to heat or vaporized water is controlled to prevent the spherical particles from bursting, while gradually releasing the water content inside the particles. Then, highly spherical shell-like crystals can be formed, while forming spherical cavities and many gaps inside.

On the other hand, the amount of air introduced or supplied into a dryer is controlled, considering the diameter, height of the drum of the dryer, the size of facilities for collection of particles such as cyclone, to prevent particles from colliding with one another, against the inner wall of the facility or from physical abrasion due to contact, in order to collect highly spherical shell-like crystals.

Consequently, it is very difficult to unify the conditions to obtain spherical particles of crystalline mannitol of the present invention, since it can be very complicated to combine the respective conditions, such as the shape of the facilities, diameter and height of the dryer, air introduction speed and temperature, the outlet diameter of the nozzle to spray the mannitol solution into mist-like drops, the diameter and shape of the atomizer, rotating speed, linear speed of discharged air flow, linear speed of collected air flow e.g. in a cyclone, often depending also the characteristics of the individual facilities.

However, to use spray dryer type ODT-20 manufactured by OHKAWARA KAKOHKI CO., LTD., spherical particles of crystalline mannitol of the present invention can be obtained, by setting the inlet temperature to be on the order of 90 to 160° C., adopting M pin type disk (diameter of 84 mmϕ manufactured by OHKAWARA KAKOHKI CO., LTD.), rotating it at a rate of 7000 to 25000 revolutions per minute, with an air blow of 5 to 15 m³/min, in order to evaporate the water at a rate of 3 to 22 kg/hr, supplied with mannitol solution at a rate of 5 to 25 kg/hr.

More detailed and concrete conditions will be explained, referring to Examples.

To keep the quality of mannitol as raw material used in the manufacturing process of spherical particles of crystalline mannitol of the present invention, appropriate crystallization speed should be respected. However, those prescribed as medicine in pharmacopoeia or satisfying the standard as food additive can be advantageously adopted. To use a spray dryer, the concentration of mannitol water solution can be advantageously set to be on the order of 5 to 35% by weight.

Spherical particles of crystalline mannitol of the present invention thus obtained have the following physicochemical properties.

Spherical particles of crystalline mannitol obtained by the present invention can be applied in various fields of foods and medicines, by making the most of the characteristics such as the excellent fluidity that could never been found conventionally, despite extremely fine particles, the three-dimensional form extremely close to perfect sphericity, as well as the presence of big cavities and gaps inside.

Spherical particles of crystalline mannitol of the present invention can be widely used e.g. as core material for spherical granules, various types of palletized or granulated powders, etc., making the most of the extremely fine particle diameter and excellent fluidity.

Spherical particles of crystalline mannitol of the present invention can be used also as a compound to carry e.g. various types of acidulants such as ascorbic acid, citric acid, malic acid, intense sweeteners such as acesulfame K, sucrarose, aspartame, various types of sugar alcohols such as maltitol, xylitol, sorbitol, erythritol, various types of flavors such as mint, vanilla, and spices, as well as various bases, food ingredients, medicines that can be contained in cavities and gaps inside the spherical mannitol.

Moreover, spherical particles of crystalline mannitol of the present invention can be very advantageously adopted also as powder to make tablets, thanks to excellent filling capacity by the presence of large cavities and gaps inside the spherical mannitol, to present high tablet hardness when directly compressed. In addition, the cavities and gaps can be filled with medicinal ingredients, various bases to make a slowly releasing product capable of adjusting the timing in elution of the medicinal ingredients, various bases inside a human body.

THE BEST MODE OF REALIZATION OF THE INVENTION

Spherical mannitol of the present invention will be explained more in detail, referring to Examples, without any intention to restrict the technical scope of the present invention to the following.

(Preparation of Mannitol Water Solution Used in Example 1)

5 parts of commercially available crystalline mannitol (Mannit P manufactured by Mitsubishi Shoji Foodtech Co., Ltd.) by weight is put into 95 parts of pure water by weight, heated till obtaining a clear solution in which solid contents have been totally dissolved, thereby making a mannitol water solution containing 5% solid matters by weight (hereinafter % meaning percentage by weight unless otherwise designated) at a temperature of 30° C., for use in Example 1.

(Preparation of Mannitol Water Solution Used in Examples 2, 3 and 5)

20 parts of commercially available crystalline mannitol (Mannit P manufactured by Mitsubishi Shoji Foodtech Co., Ltd.) by weight is put into 80 parts of pure water by weight, heated till obtaining a clear solution in which solid contents have been totally dissolved, thereby making a mannitol water solution containing 20% solid matters by weight at a temperature of 70° C., for use in Examples 2, 3 and 5.

(Preparation of Mannitol Water Solution Used in Example 4)

15 parts of commercially available crystalline mannitol (Mannit P manufactured by Mitsubishi Shoji Foodtech Co., Ltd.) by weight is put into 85 parts of pure water by weight, heated till obtaining a clear solution in which solid contents have been totally dissolved, thereby making a mannitol water solution containing 15% solid matters by weight at a temperature of 70° C., for use in Example 4.

(Preparation of Mannitol Water Solution Used in Examples 6 and 7)

30 parts of commercially available crystalline mannitol (Mannit P manufactured by Mitsubishi Shoji Foodtech Co., Ltd.) by weight is put into 70 parts of pure water by weight, heated till obtaining a clear solution in which solid contents have been totally dissolved, thereby making a mannitol water solution containing 30% solid matters by weight at a temperature of 70° C., for use in Examples 6 and 7.

(Preparation of Mannitol Water Solution Used in Example 8)

35 parts of commercially available crystalline mannitol (Mannit P manufactured by Mitsubishi Shoji Foodtech Co., Ltd.) by weight is put into 65 parts of pure water by weight, heated till obtaining a clear solution in which solid contents have been totally dissolved, thereby making a mannitol water solution containing 35% solid matters by weight at a temperature of 70° C., for use in Example 8.

(Spray Dryer Used in Examples)

Test pieces were manufactured by spray dryer of type ODT-20 (OHKAWARA KAKOHKI CO., LTD.). Mannitol solution is introduced, through a pair of Teflon (Registered Trademark) tubes (having an outer diameter of 6 mm and an inner diameter of 4 mm$\phi$), into an atomizer, placing a product collection can under itself and M-pin type disk (having a diameter of 84 mm$\phi$, manufactured by OHKAWARA KAKOHKI CO., LTD.) on itself, while hot air, jetted in a direction fixed relative to sprayed liquid to generate vortex, by parallel flow system, is introduced from above it and discharged from under it.

EXAMPLE 1

An atomizer was set to rotate at a speed of 25,000 rpm, hot air to be introduced into a spray dryer was set at a temperature of 150° C. at inlet at a rate of 14 m$^3$/minute, and 5% mannitol water solution to be introduced was set at a rate of 6.5 kg/hr. After introduction of 30 kg of mannitol water solution, prepared beforehand, powder accumulated in a product can under the spray dryer was collected and it was dried at a temperature of 80° C. for 10 minutes in a fluidized-bed dryer (FLO-5, manufactured by OKAWARA MFG. CO., LTD.). Then, spherical particles of crystalline mannitol of the present invention (Invention 1) were obtained.

Invention 1, thus obtained, has physicochemical properties and tablet hardness when directly compressed, as shown in Tables 1 and 2.

EXAMPLE 2

An atomizer was set to rotate at a speed of 25,000 rpm, hot air to be introduced into a spray dryer was set at a temperature of 100° C. at inlet at a rate of 7 m$^3$/minute, and 20% mannitol water solution to be introduced was set at a rate of 6.5 kg/hr. After introduction of 30 kg of mannitol water solution, prepared beforehand, powder accumulated in a product can under the spray dryer was collected and it was dried at a temperature of 80° C. for 10 minutes in a fluidized-bed dryer (FLO-5, manufactured by OKAWARA MFG. CO., LTD.). Then, spherical particles of crystalline mannitol of the present invention (Invention 2) were obtained.

Invention 2, thus obtained, has physicochemical properties and tablet hardness when directly compressed, as shown in Tables 1 and 2.

EXAMPLE 3

Spherical particles of crystalline mannitol of the present invention (Invention 3) were obtained, undergoing the same process as in Example 2, except for setting the atomizer to rotate at a speed of 15,000 rpm.

Invention 3, thus obtained, has physicochemical properties and tablet hardness when directly compressed, as shown in Tables 1 and 2.

EXAMPLE 4

Spherical particles of crystalline mannitol of the present invention (Invention 4) were obtained, undergoing the same process as in Example 2, except for setting the atomizer to rotate at a speed of 8,500 rpm, hot air to be introduced into the spray dryer at a temperature of 150° C. at inlet and 15% mannitol water solution to be introduced at a rate of 6.5 kg/hr.

Invention 4, thus obtained, has physicochemical properties and tablet hardness when directly compressed, as shown in Tables 1 and 2.

EXAMPLE 5

Spherical particles of crystalline mannitol of the present invention (Invention 5) were obtained, undergoing the same process as in Example 2, except for setting the atomizer to rotate at a speed of 7,000 rpm.

Invention 5, thus obtained, has physicochemical properties and tablet hardness when directly compressed, as shown in Tables 1 and 2.

EXAMPLE 6

Spherical particles of crystalline mannitol of the present invention (Invention 6) were obtained, undergoing the same process as in Example 2, except for setting the atomizer to rotate at a speed of 7,000 rpm, hot air to be introduced into the spray dryer at a temperature of 95° C. at inlet and 30% mannitol water solution to be introduced at a rate of 6.5 kg/hr.

Invention 6, thus obtained, has physicochemical properties and tablet hardness when directly compressed, as shown in Tables 1 and 2.

EXAMPLE 7

Spherical particles of crystalline mannitol of the present invention (Invention 7) were obtained, undergoing the same process as in Example 2, except for setting the atomizer to rotate at a speed of 7,000 rpm and 30% mannitol water solution to be introduced at a rate of 6.5 kg/hr.

Invention 7, thus obtained, has physicochemical properties and tablet hardness when directly compressed, as shown in Tables 1 and 2.

EXAMPLE 8

Spherical particles of crystalline mannitol of the present invention (Invention 8) were obtained, undergoing the same process as in Example 2, except for setting the atomizer to rotate at a speed of 7,000 rpm, hot air to be introduced into the spray dryer at a temperature of 115° C. at inlet and 35% mannitol water solution to be introduced at a rate of 6.5 kg/hr.

Invention 8, thus obtained, has physicochemical properties and tablet hardness when directly compressed, as shown in Tables 1 and 2.

Then, Mannit P commercially available from Mitsubishi Shoji Foodtech Co., Ltd. was used as Control 1, Pearlitol 100SD commercially available from Roquette Freres was used as Control 2, Pearlitol 200SD commercially available from Roquette Freres was used as Control 3, Parteck M200 commercially available from MERCK & CO., INC. was used as Control 4.

TABLE 1

Measurement values of mean particle diameters, loose bulk densities, angles of repose, aspect ratios, oil absorption rates and tablet hardness when manufactured at a compressing force of 1000 kgf, concerning Inventions and/or Controls

| | Controls | | | | Inventions | | | | | | | |
| --- | --- | --- | --- | --- | --- | --- | --- | --- | --- | --- | --- | --- |
| | Control 1 Mannit P | Control 2 Pearlitol 100SD | Control 3 Pearlitol 200SD | Control 4 Parteck M200 | Invention 1 (Example 1) | Invention 2 (Example 2) | Invention 3 (Example 3) | Invention 4 (Example 4) | Invention 5 (Example 5) | Invention 6 (Example 6) | Invention 7 (Example 7) | Invention 8 (Example 8) |
| Mean particle diameters (μm) | 55 | 93 | 124 | 91 | 18 | 25 | 44 | 60 | 74 | 83 | 94 | 161 |
| Loose bulk density | — | — | — | — | 0.40 | 0.47 | 0.48 | 0.40 | 0.45 | 0.44 | 0.42 | 0.38 |
| Angle of repose (degree) | — | — | — | — | 45 | 44 | 39 | 39 | 36 | 34 | 32 | 31 |
| Aspect ratio | — | — | — | — | 1.0 | 1.0 | 1.0 | 1.0 | 1.1 | 1.1 | 1.2 | 1.2 |
| Oil absorption rate 1 (%) | 8.4 | 25.6 | 23.8 | 33.5 | 40.2 | 40.7 | 31.0 | 50.9 | 53.9 | 54.0 | 50.8 | 54.1 |
| Oil absorption rate 2 (%) | 3.3 | 13.3 | 10.7 | 14.4 | 24.1 | 23.9 | 20.1 | 29.8 | 34.4 | 34.5 | 31.5 | 27.9 |
| Tablet hardness (kgf) | 3.6 | 13.1 | 5.5 | 13.6 | 17.9 | 17.2 | 16.8 | 14.5 | 13.7 | 11.5 | 8.1 | 9.5 |
| Atomizer rotating speed (rpm) | — | — | — | — | 25000 | 25000 | 15000 | 8500 | 7000 | 7000 | 7000 | 7000 |
| Inlet temperature (° C.) | — | — | — | — | 150 | 100 | 100 | 150 | 100 | 95 | 100 | 115 |
| Blast (m³/min.) | — | — | — | — | 14 | 7 | 7 | 7 | 7 | 7 | 7 | 7 |
| Liquid flow (kg/h) | — | — | — | — | 6.5 | 6.5 | 6.5 | 6.5 | 6.5 | 6.5 | 6.5 | 6.5 |
| Sprayed liquid concentration (%) | — | — | — | — | 5 | 20 | 20 | 15 | 20 | 30 | 30 | 35 |
| Sprayed liquid temperature (° C.) | — | — | — | — | 30 | 70 | 70 | 70 | 70 | 70 | 70 | 70 |

TABLE 2

Measurement values of mean particle diameters and particle size distribution concerning Inventions and Controls

| | Mean particle diameters (μm) | Cumulative percentage (%) | | | |
| --- | --- | --- | --- | --- | --- |
| | | Up to 40.4 μm | Up to 74.0 μm | Up to 248.9 μm | Up to 322.8 μm |
| Control 1 Mannit P | 55 | 35.5 | 65.1 | 98.3 | 99.43 |
| Control 2 Pearlitol 100SD | 93 | 1.02 | 22.2 | 99.6 | 100.0 |
| Control 3 Pearlitol 200SD | 124 | 2.3 | 10.6 | 97.0 | 98.9 |
| Control 4 Parteck M200 | 91 | 11.1 | 37.2 | 96.8 | 98.9 |
| Invention 1 (Example 1) | 18 | 95.2 | 99.7 | 100.0 | 100.0 |
| Invention 2 (Example 2) | 25 | 100.0 | 100.0 | 100.0 | 100.0 |
| Invention 3 (Example 3) | 44 | 39.8 | 96.3 | 100.0 | 100.0 |
| Invention 4 (Example 4) | 60 | 15.5 | 74.4 | 100.0 | 100.0 |
| Invention 5 (Example 5) | 74 | 14.1 | 50.6 | 99.7 | 100.0 |
| Invention 6 (Example 6) | 83 | 7.6 | 37.8 | 99.7 | 100.0 |
| Invention 7 (Example 7) | 94 | 9.2 | 29.2 | 99.6 | 100.0 |
| Invention 8 (Example 8) | 161 | 1.4 | 5.1 | 95.2 | 99.1 |

The measured values prove the products of the present invention to be almost spherically shaped, having a low loose bulk density and an aspect ratio of 1.2 or less, despite the fine particle diameter.

The aspect ratio of mannitol particles made by the present invention is 1.0 to 1.2, when the mean particle diameter is 15 to 165 μm, 1.0 to 1.1 when the mean particle diameter is 15 to 85 μm and 1.0 when the mean particle diameter is 15 to 65 μm, showing the values almost equal to that of perfect sphericity.

On the other hand, the products of the present invention are found to have an angle of repose within a range of 30 to 50 degrees.

Table 1 proves the products of the present invention to have great values both in oil absorption rates 1 and 2, indicating the presence of big cavities and gaps inside the particles hardly releasing oil, while proving oil absorption rate 2 of Controls to be extremely lower than that of the present invention, even though some of Controls have great values in oil absorption rate 1, indicating few cavities and gaps inside the particles.

Table 1 also shows that the products of the present invention have good hardness, when mannitol particles have a mean particle diameter of 15 to 165 μm, higher hardness, when mannitol particles have a mean particle diameter of 15 to 85 μm and the highest hardness, when mannitol particles have a mean particle diameter of 15 to 65 μm.

Also in view of the particle size distribution as shown in Table 2, good hardness is presented by the products of the present invention, when 30% or more particles have a diameter of 74 μm or less.

Some Controls present high tablet hardness, while the values of tablet hardness presented by all the products of the present invention are high enough to be used for powder to make tablets. Then, the products of the present invention can be found to be better than the Controls, all things considered also in view of the values of oil absorption rates 1 and 2 as shown in Table 1.

FIG. 1 exhibits photos of Inventions 3, 4, 6, 7 and Controls 1 to 4 taken by a scanning electron microscope (S-2600N, manufactured by HITACHI, LTD.), without metal vapor deposition, at an acceleration voltage of 20 kV, with vacuum of 50 Pa, under magnification of 1000 times (Inventions and Control 1) or of 500 times (Controls 2 to 4). As obviously shown by the photos, fine mannitol crystals are formed into spherical particles in the present invention, while relatively large particles are gathered or large crystals remain as they are in the Controls, quite unlike those of the present invention.

BRIEF EXPLANATION OF DRAWINGS

FIG. 1 It is photos of Inventions 3, 4, 6, 7 and Control 1 under magnification of 1000 times, and Controls 2 to 4 under magnification of 500 times.

The invention claimed is:

1. A powder consisting essentially of spherical particles of crystalline mannitol having an aspect ratio of 1.0 to 1.2, an oil absorption rate 1 of 25 to 60% and an oil absorption rate 2 of 15 to 40% according to test method A,
wherein the powder has a mean particle diameter of 15 to 165 μm and a loose bulk density of 0.35 to 0.60 g/mL,
wherein the test method A comprises:
adding 30 g of middle chain fatty acid triglyceride and 15 g of the powder, (together referred to hereinafter as "the sample") to a 100 ml glass beaker;
stirring the sample with a spatula gently enough to avoid crushing of fine particles;
introducing the sample into a vacuum constant temperature dryer for three hours at a room temperature at a pressure reduced down to 0.67 pascals;
pouring the sample into a centrifuge tube having openings at bottom with a filter cloth of 325 meshes laid inside;
centrifuging the centrifuge tube containing the sample by a centrifuge for 10 minutes at about 1300 G;
obtaining the weight, in grams, of the powder remaining in the centrifuge tube after centrifugation ($W_1$);
placing the centrifuge tube containing the powder remaining after centrifugation into another 100 ml glass beaker and adding 20 g of n-hexane onto the powder,
centrifuging the centrifuge tube for 10 minutes at about 1300 G;
obtaining the weight, in grams, of the powder remaining in the centrifuge tube after the second centrifugation ($W_2$),
wherein the oil absorption rate 1 and the oil absorption rate 2 are given the following formulas:

oil absorption rate 1(%)=[($W_1$−15)/15]·100 oil absorption rate 2(%)=[($W_2$−15)/15]·100.

2. The powder of claim 1, wherein the powder has an angle of repose of 30 to 50 degrees.

3. The powder of claim 1, wherein the powder has a mean particle diameter of 15 to 85 μm.

4. The powder of claim 1, wherein the powder has a mean particle diameter of 15 to 85 μm and an angle of repose of 30 to 50 degrees.

5. The powder of claim 1, wherein the powder has a mean particle diameter of 15 to 65 μm.

6. The powder of claim 1, wherein the powder has a mean particle diameter of 15 to 65 μm and an angle of repose of 30 to 50 degrees.

7. The powder of claim 1, wherein the spherical particles have a hardness of 7 to 20 kgf, when directly compressed.

8. The powder of claim 1, wherein the spherical particles are made by spray drying.

* * * * *